US012643105B2

(12) United States Patent
Blaire et al.

(10) Patent No.: US 12,643,105 B2
(45) Date of Patent: Jun. 2, 2026

(54) METHOD AND DEVICE FOR COLLECTING AND ANALYSING AIRBORNE PARTICLES

(71) Applicant: Commissariat à l'Energie Atomique et aux Energies Alternatives, Paris (FR)

(72) Inventors: Guillaume Blaire, Grenoble Cedex (FR); Manuel Alessio, Grenoble Cedex (FR); Mélissa Baque, Grenoble Cedex (FR); Jean-Maxime Roux, Grenoble Cedex (FR)

(73) Assignee: Commissariat à l'Energie Atomique et aux Energies Alternatives, Paris (FR)

( * ) Notice: Subject to any disclaimer, the term of this patent is extended or adjusted under 35 U.S.C. 154(b) by 730 days.

(21) Appl. No.: 18/065,007

(22) Filed: Dec. 13, 2022

(65) Prior Publication Data

US 2023/0191410 A1 Jun. 22, 2023

(30) Foreign Application Priority Data

Dec. 17, 2021 (FR) ..................................... 21 13752

(51) Int. Cl.
*B01L 3/00* (2006.01)
*B01L 7/00* (2006.01)
(Continued)

(52) U.S. Cl.
CPC .......... *B01L 3/502761* (2013.01); *B01L 7/52* (2013.01); *C12Q 1/6844* (2013.01);
(Continued)

(58) Field of Classification Search
None
See application file for complete search history.

(56) References Cited

U.S. PATENT DOCUMENTS 5,198,749 A * 3/1993 Guthrie .............. G01N 33/2025
164/4.1
10,161,835 B1 12/2018 Moorman et al.
(Continued)

FOREIGN PATENT DOCUMENTS

WO WO 2005/089108 A2 9/2005

OTHER PUBLICATIONS

French Preliminary Search Report and Written Opinion Issued Aug. 18, 2022 in French Application 21 13752 filed on Dec. 17, 2021 (with English Translation of Categories of Cited Documents), 11 pages.

*Primary Examiner* — Brian R Gordon
(74) *Attorney, Agent, or Firm* — Oblon, McClelland, Maier & Neustadt, L.L.P.

(57) ABSTRACT

A method for collecting and analysing airborne particles, including a step of eluting particles precipitated on a collecting surface, a step of analysing the airborne particles collected in the reaction chamber, the eluting step being carried out by heating a first reservoir containing the elution liquid to a first temperature value, the analysing step being carried out by heating the reaction chamber to a second temperature value higher than the first temperature value, so as to: activate a detection reaction in the reaction chamber, isolate the reaction chamber during the detection reaction, initiate a device for sealing the reaction chamber, a step of sealing the reaction chamber.

7 Claims, 10 Drawing Sheets

(51) Int. Cl.

| | |
|---|---|
| *C12Q 1/6844* | (2018.01) |
| *G01N 1/22* | (2006.01) |
| *C12Q 1/6806* | (2018.01) |

(52) U.S. Cl.

CPC .... *G01N 1/2202* (2013.01); *B01L 2200/0652* (2013.01); *B01L 2200/16* (2013.01); *B01L 2400/0677* (2013.01); *C12Q 1/6806* (2013.01); *G01N 2001/222* (2013.01)

(56) References Cited

U.S. PATENT DOCUMENTS

| | | | |
|---|---|---|---|
| 11,335,910 B1 * | 5/2022 | Suttil | H01M 4/368 |
| 2003/0006140 A1 * | 1/2003 | Vacca | G02B 6/3538 |
| | | | 204/600 |
| 2004/0232052 A1 | 11/2004 | Call et al. | |
| 2012/0174650 A1 | 7/2012 | Ariessohn et al. | |
| 2013/0042893 A1 | 2/2013 | Ariessohn et al. | |
| 2019/0154550 A1 * | 5/2019 | Wu | G01N 33/56983 |
| 2023/0011524 A1 * | 1/2023 | Molyneux | C12Q 1/6844 |
| 2023/0027503 A1 * | 1/2023 | Liu | G01N 1/2205 |
| 2023/0272202 A1 * | 8/2023 | Hartwig | C08G 61/08 |
| | | | 525/191 |
| 2024/0226887 A1 * | 7/2024 | Kim | B01L 7/52 |

* cited by examiner

METHOD AND DEVICE FOR COLLECTING AND ANALYSING AIRBORNE PARTICLES

TECHNICAL FIELD OF THE INVENTION

The present invention relates to a method and device for collecting and analysing airborne particles.

PRIOR ART

A number of solutions for precipitating particles present in an aerosol, with the aim of analysing these particles, have already been proposed in the prior art.

One known and particularly advantageous separating method is electrostatic. It is implemented in electrostatic precipitators (ESPs), which are also called electrostatic filters.

There are a number of categories of electrostatic precipitators, among which:

so-called dry electrostatic precipitators, which are for example described in patent application WO2015/197747A1, so-called wet electrostatic precipitators, which are for example described in patent application WO2004/041440A1, so-called semi-wet electrostatic precipitators, which are for example described in patent application WO2007/012447A1.

In all these categories, the precipitators comprise a chamber into which is injected or sucked an air stream containing the particles, and generate an electric field between two electrodes: a discharge electrode and a counter-electrode that is called the collecting electrode, which is in general connected to ground.

The electric field created between the two electrodes generates a flux of ions from an ionized pocket of gas encircling the discharge electrode. The air stream containing the particles is injected through the flux of ions. In the presence of ions, the particles acquire an electric charge and thus become sensitive to the electric field generated between the two electrodes and are driven by electric force towards the counter-electrode.

In the first category of electrostatic precipitators (so-called dry electrostatic precipitators), the precipitated particles are detached from the collecting electrodes using a dry process, for example one employing vibration of the electrodes or even mechanical brushes brushed over the surfaces of the latter.

In the second category of electrostatic precipitators (so-called wet electrostatic precipitators), the particles captured on the collecting electrode are removed by trickling water over the latter.

In the third category of electrostatic precipitators (so-called semi-wet electrostatic precipitators), water vapour is introduced into the chamber containing the discharge electrode or upstream thereof. The particles in suspension in the air then cross via heterogeneous nucleation to form droplets and said droplets are precipitated on the counter-electrode via the electric force. The introduced vapour may furthermore condense on the walls and then trickle over the collecting electrode, which contributes to the removal of the captured particles.

The publication referenced "Hyeong Rae Kim, Sanggwon An, and Jungho Hwang, *Aerosol-to-Hydrosol Sampling and Simultaneous Enrichment of Airborne Bacteria For Rapid Biosensing, ACS Sens.* 2020, 5, 2763-2771" describes a recent example of an electrostatic precipitator intended to precipitate bio-particles from an air stream. The air stream is injected into a channel and passes between two electrodes. The particles in suspension in the air are attracted towards the collecting electrode via electrostatic precipitation. A liquid is continuously injected to elute the particles captured on the collecting electrode. This solution notably requires a continuous flow of liquid to elute the particles present on the collecting electrode, this meaning that this solution is not easily adaptable to use in an instrument borne by or deployed with a drone for example. Specifically there is a risk, in operation, of the elution liquid dispersing and flowing into the air channel if the device is tilted. The liquid could also form a bridge between the electrodes if the device were flipped, short-circuiting the two electrodes. The same problem arises with the technical solutions described in the aforementioned patents WO2004/041440A1 and WO2007/012447A1.

Another problem that arises with the existing solutions regards reuse of the same precipitating device. If pathogens are precipitated during a sampling operation, it is necessary to decontaminate all the surfaces on which they have deposited. However, the channel through which the air flows, the electrodes and the tubes employed to deliver the elution liquid and to convey it to a collection chamber are difficult to access. It would be advantageous to provide a technical solution that would allow samples to be taken one after another, without having to decontaminate the precipitating and eluting device.

Generally, the precipitated and eluted particles are extracted from the precipitator with a view to being analysed in an external chamber. The external chamber possesses all the features allowing a reliable analysis of these particles to be carried out, for example via (PCR, LAMP, etc.) biomolecular amplification. An operator is often tasked with this transfer, and with making sure that the reaction conditions used, notably in respect of temperature, are the right ones.

All the existing completely integrated and quasi-autonomous solutions in which the particles are automatically delivered to a chamber to be analysed are complex. By way of example, the publication referenced "X. Jiang, J.C. Loeb, M. Pan et al., *Integration of sample preparation with RNA-Amplification in a handheld device for airborne virus detection, Analytica Chimica Acta* 1165 (2021) 338542" describes a device and method allowing particles in suspension in the air to be precipitated, reagents to be delivered, and the presence of pathogens to be detected via biomolecular amplification. However, the device comprises a great many components, which must be installed before use and, between two sampling and analysing operations, must be uninstalled and notably separated from the precipitating device to be replaced. The addition of the reagents required to carry out the analyses also comprises a manual rotation step. Although this step could be automated, a motor and mechanical links would be required to do so, and these would further complexify the device.

Documents US2012/174650A1, WO2005/089108A2 and U.S. Pat. No. 10,161,835B1 describe solutions for collecting and analysing airborne particles.

The aim of the invention is to provide a method and device for precipitating, collecting and analysing airborne particles, in which device airborne particles may be collected and analysed simply and reliably, without risk of dispersion of the elution liquid in operation, and without use of complex means such as mechanical links to carry out the steps of sample preparation and analysis, and without risk of transfer of contamination from one sample to another.

SUMMARY OF THE INVENTION

This aim is achieved via a method for collecting and analysing airborne particles, comprising:

a step of eluting particles precipitated on a collecting surface, by injecting an elution liquid through an elution fluidic circuit, said elution fluidic circuit being arranged to convey said precipitated particles to a reaction chamber of an analysis module, a step of analysing the airborne particles collected in the reaction chamber, the eluting step being carried out by heating a first reservoir containing said elution liquid to a first temperature value in order to make a first meltable compound melt, maintaining said first reservoir under pressure, the analysing step being carried out by heating the reaction chamber to a second temperature value higher than the first temperature value, so as to:

activate a detection reaction in said reaction chamber with a view to carrying out an analysis of the airborne particles, isolate said reaction chamber during the detection reaction by activating a device for isolating the reaction chamber, initiate a device for sealing the reaction chamber, by melting a second meltable compound, a step of sealing said reaction chamber by setting the second meltable compound, which occurs when the temperature drops to a third value lower than said second value.

According to one particularity, the method comprises a step of controlling the reaction by injecting a second elution liquid into at least one control chamber identical to said reaction chamber.

According to another particularity, each elution liquid contains reagents used in the reaction in the reaction chamber.

According to another particularity, the reaction is a bio-molecular-amplification reaction.

According to another particularity, the activation of the device for isolating the reaction chamber consists in closing a first isolation valve arranged in the elution fluidic circuit and equipped with a deformable membrane.

According to one particular embodiment, initiation of the device for sealing the reaction chamber consists in releasing the second meltable compound into the elution fluidic circuit.

According to another particular embodiment, initiation of the device for sealing the reaction chamber consists in releasing the second meltable compound so that the latter deposits on the deformable membrane of the first isolation valve.

The invention also relates to a device for collecting and analysing airborne particles and suitable for implementing the method such as defined above, the device comprising:

a module for eluting particles precipitated on a collecting surface, by injecting an elution liquid through an elution fluidic circuit, said elution fluidic circuit being arranged to convey said precipitated particles to a reaction chamber of an analysis module, a module for analysing airborne particles collected in the reaction chamber, the eluting module comprising a first reservoir into which is injected the elution liquid maintained under pressure by a first meltable compound, said first meltable compound being chosen for its ability to melt as a result of a first operation of heating to a first temperature value, with a view to releasing said elution liquid, the analysing module comprising:

a device for isolating the reaction chamber, said device being configured to isolate said reaction chamber on a second operation of heating the reaction chamber to a second temperature value higher than said first temperature value, a device for sealing the reaction chamber, said device being initiated by melting a second meltable compound configured to set at a third value lower than said second value.

According to one particularity, the device comprises a reaction-controlling module comprising at least one control chamber identical to said reaction chamber and into which is injected a second elution liquid.

According to another particularity, each elution liquid contains reagents used in the reaction in the reaction chamber.

According to another particularity, the reaction is a bio-molecular-amplification reaction.

According to another particularity, the device for isolating the reaction chamber comprises a first isolation valve arranged in the elution fluidic circuit and equipped with a deformable membrane.

According to one particular embodiment, the device for sealing the reaction chamber comprises a body of the second meltable compound positioned to be released into the elution fluidic circuit on initiation.

According to another particular embodiment, the device for sealing the reaction chamber comprises a body of the second meltable compound positioned to deposit on the deformable membrane on initiation.

According to one particularity, the device comprises a component for precipitating and analysing airborne particles, said component taking the form of an element of integral construction, comprising:

a module for precipitating airborne particles;

the module for eluting the precipitated airborne particles;

the module for analysing the particles eluted to the reaction chamber.

According to another particularity, the device comprises a heating module taking the form of an instrument into which said precipitating and analysing component is removably fitted.

BRIEF DESCRIPTION OF THE FIGURES

Other features and advantages will become apparent from the detailed description, which is given with reference to the appended drawings, in which:

FIG. 9 schematically shows one advantageous variant of embodiment of the component of the invention.

DETAILED DESCRIPTION OF AT LEAST ONE EMBODIMENT

In the rest of the description, the terms "upstream" and "downstream" are to be understood with reference to the direction of flow of the fluid through the fluidic circuit in question.

In the rest of the description, a valve in the open state lets fluid pass (state 1 or ON) and a valve in the closed state prevents fluid from passing (state 0 or OFF).

A complete system allowing airborne particles to be precipitated, the precipitated particles to be collected and the particles to be analysed comprises a plurality of functional modules:

a module M1 for precipitating airborne particles;
a fluidic module M2 for eluting the precipitated airborne particles;
a module M3 for analysing particles eluted to a reaction chamber;
a heating module M4, which is common to a plurality of said other modules;
a control module M5, which is configured to command the various operational modules of the component.

Figure 1:
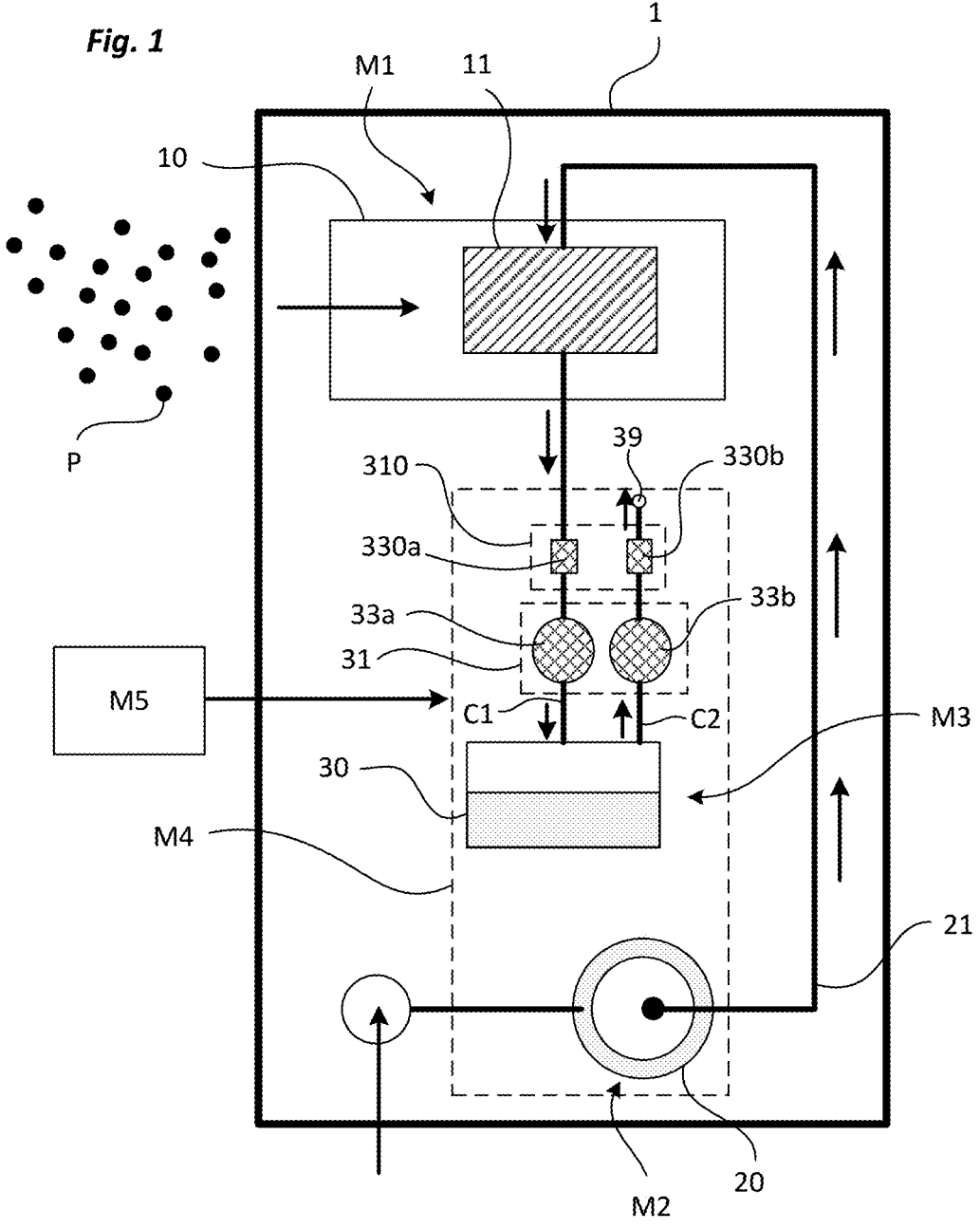
FIG. 1 schematically shows a component for precipitating and analysing airborne particles that is according to the invention and that is suitable for implementing the method of the invention.

FIG. 1 shows a precipitating and analysing component 1 capable of implementing certain steps of a precipitating and analysing method in this component.

The precipitating and analysing component 1 advantageously takes the form of an element of integral construction, for example containing a plurality of the aforementioned functional modules, and notably:

the module M1 for precipitating airborne particles;
the fluidic module M2 for eluting the precipitated airborne particles;
the module M3 for analysing particles eluted to a reaction chamber.

The heating module M4 is common to a plurality of said other modules and advantageously forms part of an instrument into which the component may be fitted. In the appended figures, the module M4 has been represented by a region bounded by a dashed line, corresponding to its region of influence on the modules of the component 1.

Likewise, the control module M5, which is configured to command the various operational modules of the component with a view to collecting the particles P and to analysing the particles, advantageously forms part of the aforementioned instrument.

With the aim of producing an entirely autonomous monitor, the heating module M4 may however be integrated into the component or be assembled therewith. The same goes for the control module M5. In this case, the system will possibly also comprise an electrical power source such as an on-board battery.

The term "module" must be understood to mean one or more hardware and potentially software components or elements allowing one or more steps of the method of the invention to be carried out.

The particles P may be micro-particles or nano-particles, whether biological or not, present in suspension in the air in the form of an aerosol.

Non-limitingly, the particles P may notably be precipitated from ambient air or from the air expired by a living being. In the rest of the description, the particles in question are precipitated from ambient air.

One of the objectives is to analyse the particles P with a view to detecting the presence of a pathogenic agent or a trace of its presence.

The solution may have the following particularities:

The sought pathogenic agents may be, inter alia, microorganisms such as viruses, bacteria, fungal spores, toxins, mycotoxins, allergens, or any other harmful agent.

The particles P are advantageously precipitated with the aim of analysis. The analysis may consist in detecting the presence: of DNA; of RNA; of proteins; of component elements of the pathogenic agent, such as lipids or carbohydrates; of one or more pathogenic agents present in the collected particles. The analysis may also consist in detecting molecules such as ATP or even sugars such as mannitol, arabitol and glucose, which provide information on the presence of microorganisms. The analysis may also regard detection of molecules such as allergens and mycotoxins.

By way of example, the analysing method may be a biomolecular-amplification method (for example LAMP, RPA, PCR, etc.), an immuno-enzymatic method (for example ELISA) or an immunochromatographic method (for example ICS).

The component 1 will possibly, notably, be employed in the form of an area monitor. To be so employed, it will then need to have a certain autonomy in operation, i.e. to be able to precipitate and analyse the particles with a minimum of exterior intervention.

The precipitating module M1 advantageously works via the electrostatic effect. Non-limitingly, it may comprise two electrodes: a discharge electrode connected to an electrical potential, and a counter-electrode that is called the collecting electrode, which is in general connected to ground. The two electrodes are spaced apart from each other so as to create a sufficient electrostatic field to attract the airborne particles P towards the collecting electrode, said particles being intended to be captured and trapped on a collecting surface associated with this collecting electrode.

The precipitating module may notably comprise a precipitation channel 10 into which is injected or sucked an air stream containing the particles. Precipitating means that generate the air stream are for example configured to direct the particles P present in the air towards the collecting electrode contained in said precipitating channel 10. The flow of air through the channel 10 may be forced (for example using a fan) or not. The particles P may be collected on a membrane 11, forming the collecting surface and possibly incorporating the collecting electrode.

The component 1 may also incorporate an eluting fluidic module M2 (the eluting module below) comprising at least one elution circuit. This elution circuit comprises an eluent reservoir 20 and an elution fluidic channel 21 that opens at one end into the reservoir and at the other end onto the collecting surface. It is used to convey the elution liquid to the collecting surface and allows the elution liquid to be poured onto the collecting surface with a view to detaching the particles P and transporting them to the analysing module M3.

The eluent reservoir 20 advantageously contains the elution liquid, for example a liquid such as water, this fluid allowing particles collected from the collecting surface to be placed in suspension. The elution liquid may also contain at least some of the reagents required to achieve the detection reaction in the analysis chamber.

Figures 2, 3:
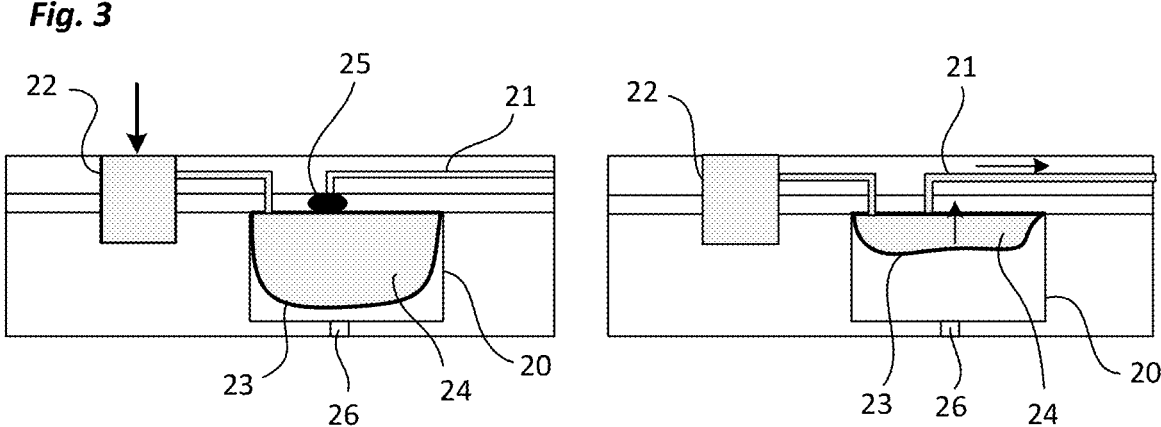
FIG. 2 schematically shows the principle of production of the eluting module used in the component of the invention.
FIG. 3 illustrates, via cross-sectional views, the principle of operation of the eluting module of FIG. 2.

As shown in FIG. 2 and FIG. 3, the eluting module M2 may comprise an inlet port 22 blocked by a septum, via which is injected the elution liquid 24 towards its reservoir 20. The eluting module M2 may comprise a deformable membrane 23 housed in the reservoir 20 and able to deform towards the interior of the reservoir 20 under the pressure of the elution liquid 24 injected via the inlet port 22. The reservoir 20 is initially sealed by a deposit of a first meltable compound 25, forming a plug, thus allowing it to be placed under pressure during the injection of the fluid 24. Under the membrane 23, the eluting module advantageously comprises a vent 26, intended to allow the air present to escape when the reservoir 20 is placed under pressure. The presence of the vent 26 notably allows a calibrated and reproducible volume to be obtained in the reservoir 20.

The first meltable compound 25 may be deposited in the form of a ball, for example using a micro-pipette, in order to isolate the reservoir from the elution fluidic channel. This ball is deposited in liquid form. To industrialize this process, a pipetting robot could be used, or the first meltable material deposited in solid form followed by local heating. On cooling, this ball of the meltable compound sealably closes the communication between the chamber and the elution fluidic channel. A seal, a silicone seal or any other type of seal, may be inserted between the outlet of the reservoir 20 and the meltable compound, in order to compensate for any differences in expansion between the meltable material and the material encircling the via used to access the reservoir 20.

At the outlet of the reservoir, the eluting module may comprise a region 27 for trapping the meltable compound. This region takes the form of a flared portion of the elution fluidic channel 21. The volume of meltable compound used must be smaller than the volume of the region for trapping the material.

The meltable compound may be a paraffin wax, capable of melting at a first temperature. For example, 2 μL of paraffin wax is deposited for a trapping-region volume of 4 μL.

The operating principle of the eluting module is as follows:

The reservoir 20 being sealed by the plug produced by the first meltable compound 25, the elution liquid 24 is injected through the septum 22. This injection of fluid 24 places the reservoir 20 under pressure, thereby deforming the membrane 23. Under this membrane, which is made of silicone, the vent 26 allows the air present before filling to escape. Typically, a volume of 100 μL is injected into the reservoir 20. The membrane 23, which is very deformable, conforms to the shape of the reservoir 20, thus allowing this reservoir 20 to be filled with a calibrated and reproducible volume.

The control module M5 present in the instrument employing the component 1 activates the heating module M4 of the instrument in order to heat the first meltable compound 25 present in the component 1 to above its melting point. For example, if the meltable compound is a paraffin wax such as docosane (melting point=45° C.) it will be heated to a temperature of 48° C.

As soon as the first meltable compound 25 melts, it flows and finds itself pushed by the pressure present in the reservoir 20 into the elution fluidic channel 21. The trapping region 27, which is still at low temperature because outside of the region of influence of the heating module M4, allows, via its flared shape, the speed of the fluid to be slowed therein and provides a region the volume of which is large enough to store the first meltable compound, which solidifies therein. The latter, on cooling, preferentially sets on the walls of the elution fluidic channel 21, in its flared portion, while leaving a space large enough to allow the elution liquid 24 to flow through the elution fluidic channel 21. Pressure is maintained in the channel by the membrane 23 and allows the fluid to reach the precipitating module M1, without other means.

In one variant of embodiment, the vent 26 may be connected to a closed second reservoir. This reservoir is placed under pressure when the membrane 23 is deformed by the fluid. The membrane 23 may be completely deformed, guaranteeing volume since the air will be compressed in this second reservoir. It is thus possible to increase the pressure in the reservoir 20, and to make it so that this pressure is calibrated (by the size of the second reservoir) and so that a calibrated volume of liquid is obtained.

As indicated above, the module M3 for analysing the precipitated particles P is advantageously also integrated into the component 1, in order to decrease the hardware that an operator has to manipulate and thus automate the method.

The analysing module M3 mainly comprises a reaction chamber 30 into which the elution fluidic channel 21 opens and advantageously a channel opening onto the exterior to form a vent 39.

The reaction chamber 30 is advantageously formed in the component. This reaction chamber 30 may contain at least some of the reagents required to perform the analysis, and for example to achieve an amplification reaction or equivalent.

As mentioned above, the analysis may be carried out via biomolecular amplification or be an immuno-enzymatic analysis (e.g. ELISA).

An analysis via biomolecular amplification of microorganisms assumes extraction of the genomic material from the microorganisms. Various technical solutions may of course be used to do this. Advantageously, the microorganisms are lysed thermally, and thus the heating module M4 of the system serves not only for the elution of the precipitated microorganisms, optionally for the lysis that leads to the extraction of the genomic material, but also for the biomolecular amplification. By way of example, a step of heating the chamber 30 to 65° C. allows the genetic material of certain viruses to be extracted.

Under certain conditions, it is necessary to isolate or even seal the chamber 30, whether during the detection reaction, to avoid evaporation of the solution during the heating step required by the biomolecular amplification, or to avoid contaminating the mixture, or even to ensure safe transport of the component 1.

Figure 4:
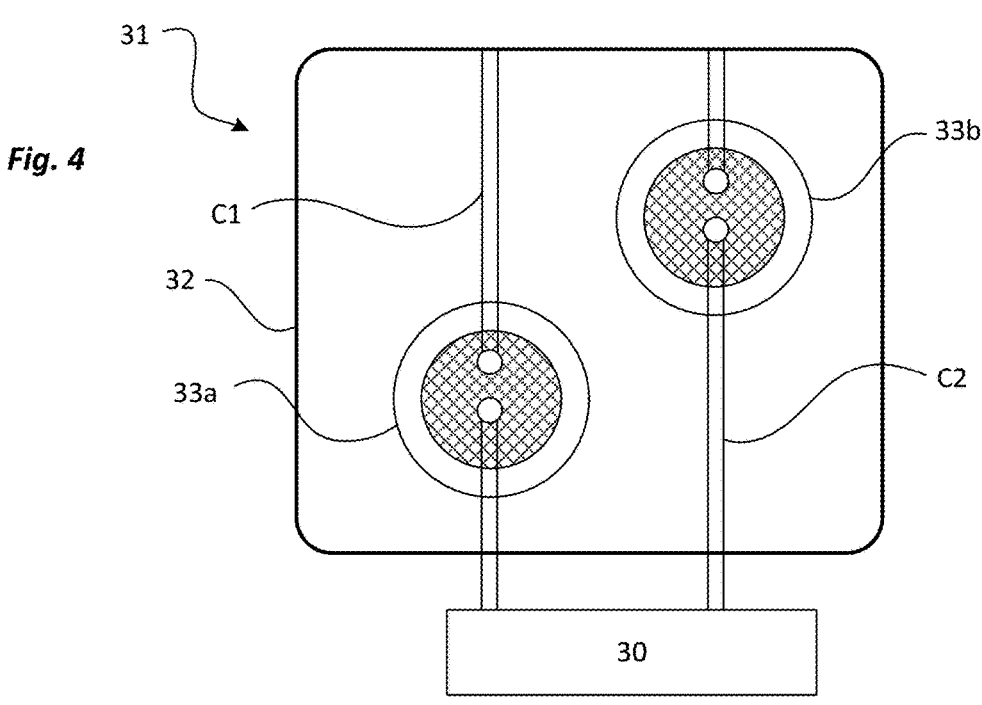
FIG. 4 schematically shows the principle of production of the isolating device employed in the component of the invention.
Figure 5:
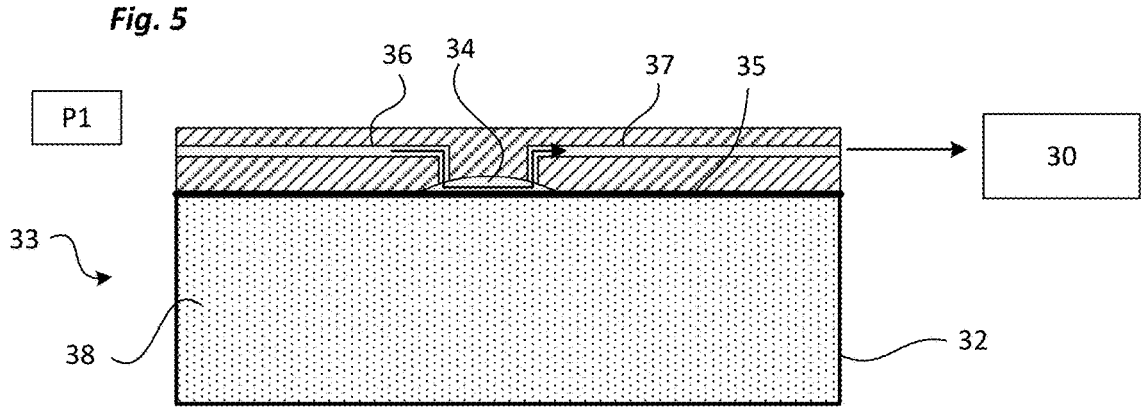
FIG. 5 illustrates, via cross-sectional views, the principle of operation of the isolating device of FIG. 4.
Figure 5:
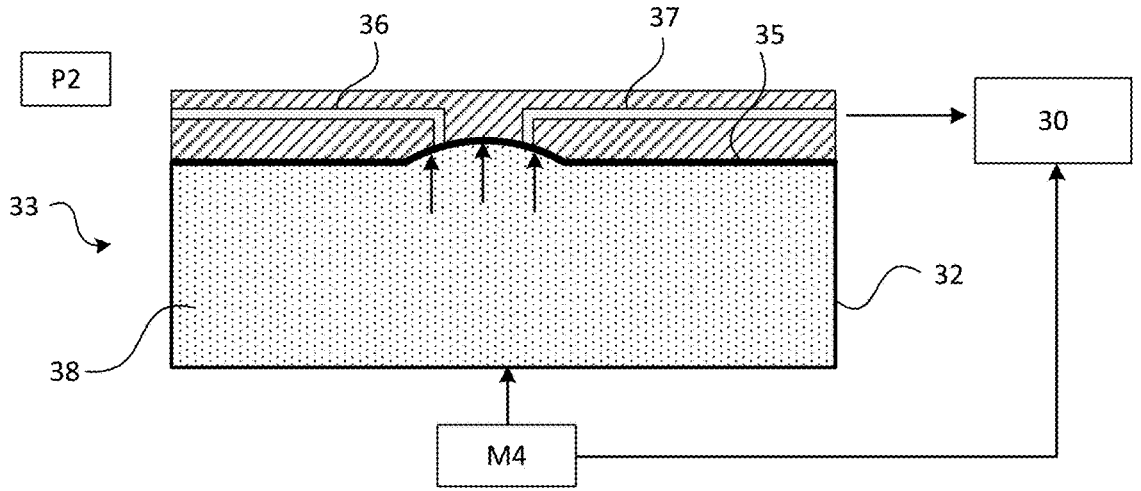

According to the invention, with reference to FIG. 4 and FIG. 5, the analysing module M3 comprises a device 31 for isolating the reaction chamber 30.

This isolating device 31 is advantageously common to both fluidic circuits opening into the reaction chamber 30, i.e. to the elution fluidic circuit C1 and to the fluidic circuit C2 comprising the vent 39.

It comprises at least one reservoir 32 intended to contain a volume of air 38 and one separate isolation valve 33a, 33b (reference 33 generally) for each fluidic circuit. The chosen reservoir 32 of air is common to the two valves 33a, 33b, but use of two separate reservoirs could be envisaged.

With reference to FIG. 5, each isolation valve 33 comprises a space 34 into which opens an inlet channel 36 and from which exits an outlet channel 37 leading to the reaction chamber 30, the volume of the space 34 varying depending on the position of a deformable membrane 35. The membrane 35 is able to deform between a first position, called the open position, in which it lets the fluid pass into the controlled circuit (FIG. 5—P1) and a position, called the closed position, in which it prevents the fluid from passing into the controlled circuit (FIG. 5—P2). In its closed position, the volume of the space 34 is zero or almost zero, the membrane 35 being pressed against a surface onto which the two channels open. Depending on its position, the membrane 35 therefore allows the volume of the space 34 of the isolation valve 33 to be modulated.

To move the membrane 35 between its first position and its second position, the heating module M4 is used. The heating module M4 is arranged and configured to heat the volume of air 38 placed in the reservoir 32 in order to cause this volume of air to dilate. On dilating in the reservoir 32, the air pushes against the membrane 35, deforming it towards its closed second position (P2). The membrane 35 thus closes off the two channels 36, 37 in order to close the fluidic circuit.

It will be noted that the reservoir 32 is closed in a seal-tight manner in the component.

Advantageously, the activation of the heating module M4, required to drive the detection reaction in the reaction chamber 30, is used to actuate the membranes 35 of both valves 33a, 33b to their closed position and thus to isolate the chamber 30 by closing both fluidic circuits. In other words, to hot isolate the reaction chamber 30 using the two valves 33a, 33b and to drive the detection reaction the heating module M4 need receive only one command. By way of example, this reaction takes place at 65° C. in the case of LAMP. The material and the geometric characteristics of the membrane 35 are then chosen so as to obtain closure of the valves at 65° C.

More concretely, the operating principle of the device 31 is as follows:

At room temperature, the chamber 30, the chamber 32 and the two fluidic circuits are at similar pressures. The membrane 35 is in its open position (P1), and the elution liquid may thus pass freely.

When the heating module M4 is activated, the air contained inside the reservoir 32 dilates. To a first approximation, the increase in pressure is directly proportional to the increase in temperature (in K). Thus, on passing from 25° C. to 65° C. (298 K to 338 K) the pressure increases by 13% (about 100 mbar), this greatly deforming the membrane 35 of each valve 33.

In each valve 33, the deformed membrane 35 then blocks the two channels of the fluidic circuit, isolating the reaction chamber 30 from the exterior (P2).

One very beneficial advantage of this device is that it prevents any dilation of air bubbles potentially found in the reaction chamber 30. Specifically, a bubble in the reaction chamber 30 will see the same pressure increase as the membrane 35, because it will also see the same increase in temperature. With such a device, the size of the bubble in the chamber will therefore not be able to vary during heating.

This device, by closing the two fluidic circuits leading to the reaction chamber 30, also allows evaporation to be greatly limited. Thus, analyses of 30 min may be carried out without loss of liquid.

When the temperature decreases again, the pressures between the reservoir 32 and the fluidic circuits equilibrate and the membrane 35 returns to its original open position (P1).

According to another aspect of the invention, a cold device for sealing the chamber 30 is used, once the detection reaction has ended.

In the context of a biomolecular-amplification detection reaction, it is indispensable to be able to isolate the reaction volume after analysis, in order to avoid any contamination, by sealing the reaction chamber 30. Specifically, if RNA/DNA molecules are present in the sample to be analysed, their quantity will be amplified by several orders of magnitude by the reaction. The number of amplicons after analysis may therefore be very high. It is absolutely necessary to avoid any leakage of liquid containing amplicons, as otherwise the risk that the instrument and its environment will be irremediably contaminated is run.

Two variants of embodiments of this sealing device are described below.

Figure 6A:
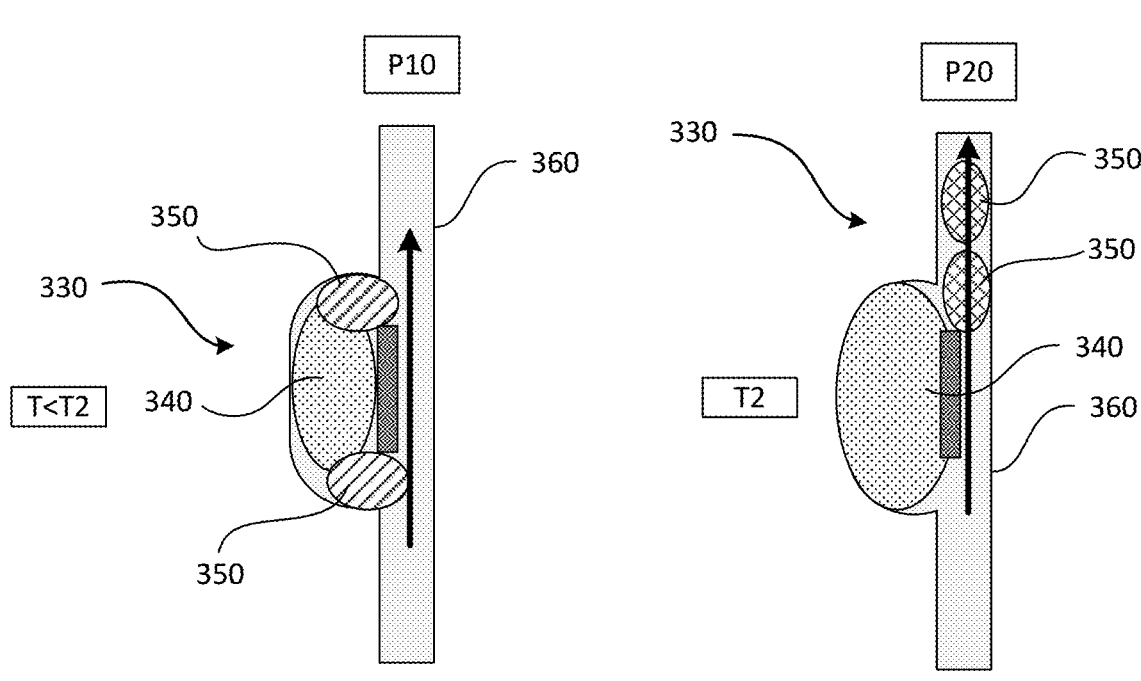
FIG. 6A schematically illustrates the principle of operation of the sealing device used in the component of the invention.
Figure 6A:
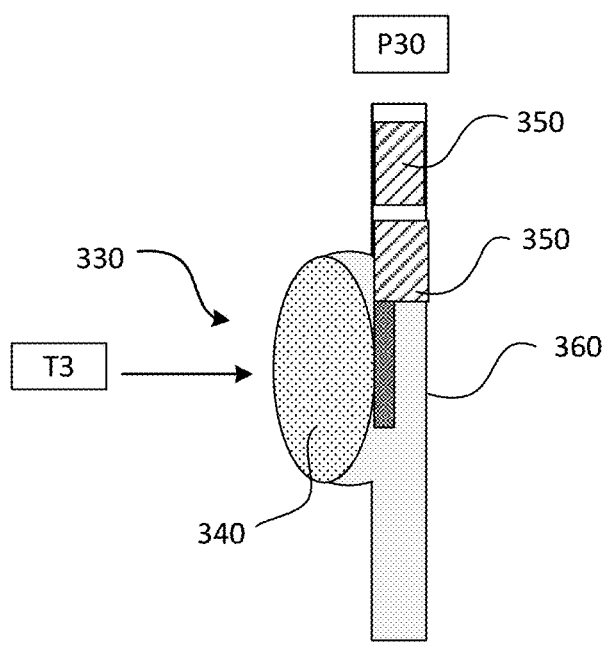

In a first variant embodiment, illustrated in FIG. 6A, the sealing device 310 comprises two cold sealing valves 330a, 330b (reference 330 generally) integrated into the component.

In the elution fluidic circuit C1, the first cold sealing valve 330a is positioned upstream of the first hot isolating valve 33a described above (see FIG. 1).

In the fluidic circuit C2 comprising the vent 39, the second cold sealing valve 330b is positioned downstream with respect to the second hot isolating valve 33b described above (see FIG. 1).

It will be noted that the second sealing valve 330b, placed in the fluidic circuit C2 comprising the vent 39, is not indispensable—the vent 39 could be equipped with a hydrophobic barrier membrane.

With reference to FIG. 6A, each valve 330 is composed of at least two bodies 350 of a second meltable compound, initially trapping an element capable of dilating, in the channel 360 of the fluidic circuit in question, an air bubble 340 for example. Small volumes of this second meltable compound are deposited, for example using a pipette, in defined locations on the edge of the channel in question. The air bubble 340 also has a defined location between the two bodies 350 of meltable compounds in each channel in the micro-fluidic circuit. These locations may for example be defined by machining by means of a cutter, or by laser etching, or even when the circuit is moulded.

The melting point of the second meltable compound is chosen to be higher than the temperature value T1 employed to activate the eluting module M2 described above, and also higher than or equal to the temperature value T2 applied to the device 31 for controlling fluidic access and to the chamber 30. The second meltable compound may also be a paraffin wax with a melting point of 55° C. (the chosen paraffin wax is for example tetracosane). The second meltable compound is chosen to have a melting point higher than that of the first meltable compound 25 used in the eluting module M2, in order to prevent it from melting during the activation of the eluting module M2.

The operating principle of this sealing device 310 is as follows:

Below its melting point, and therefore during the steps described above of injecting the eluent and therefore of eluting the precipitated particles, the two bodies 350 remain trapped on the edge of the channel: the liquid may flow freely (FIG. 6A—P10).

Above its melting point (at the temperature T2), the second meltable compound forming the two bodies 350 melts, and the air bubble 340, which is under pressure as a result of the applied heat, may dilate, pushing the two molten bodies 350 into the channel. There is no pressure in the main channel other than hydrostatic pressure, and the molten plugs, which are subject to buoyant force and to capillary forces, remain liquid for the duration of the heating required by the analyses (30 minutes for example). Experimentally, the two molten bodies are thus observed to rise slightly in the channel (paraffin wax being less dense than water), the geometry of the valve promoting this rise (FIG. 6A—P20) in the channel 360.

On cooling (at the temperature T3), this slight rise of the bodies 350 is sufficient for, on contraction of the air bubble 340, liquid coming from the reaction chamber 30 to fill the available space, letting a good portion of the second meltable compound solidify in the channel (FIG. 6A—P30).

At high temperature, i.e. above the melting point T2, as they float in the channel 360 above the reaction chamber 30, the molten bodies 350 contribute to limiting evaporation of the liquid.

At low temperature, i.e. below the melting point T2, after the chamber 30 has been heated or even after the heating cycle, the second meltable compound returns to the solid state and the bodies 350 completely seal the various channels, isolating any amplicons from the exterior medium. Such valves, which isolate the reaction chamber 30 on return to room temperature, allow a seal to be guaranteed under any circumstances, whether a handling error or even a malfunction of the instrument.

Figure 6B:
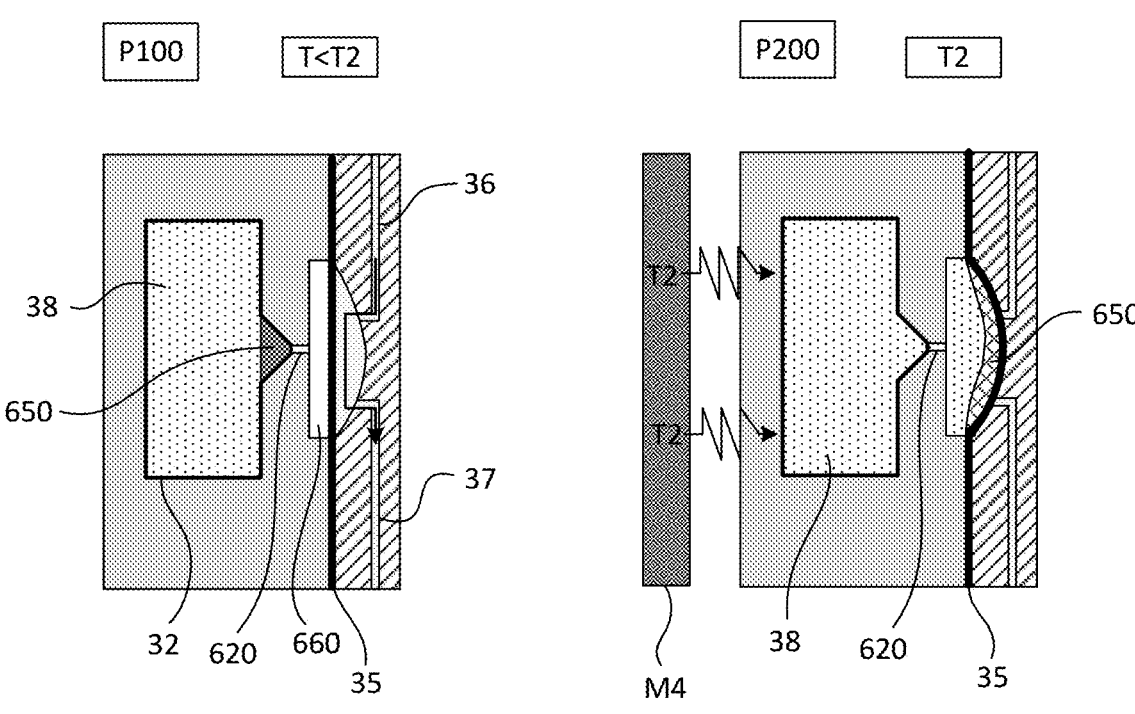
FIG. 6B schematically illustrates the principle of operation of one variant of embodiment of the sealing device used in the component of the invention.
Figure 6B:
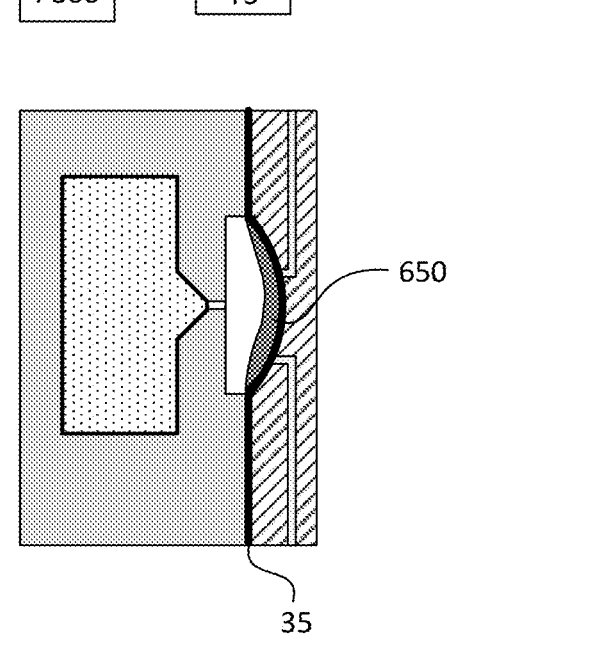

With reference to FIG. 6B, the second variant of the sealing device is as follows.

This sealing device has the particularity of being incorporated into the isolating device 31 that was described above and thus complements this already described isolating device 31 and adds thereto the sealing function.

The sealing device thus comprises a fluidic channel 620 that opens on one side into the internal space of the reservoir 32, which is filled with the volume of air 38, and on the other side into a space 660 closed by the membrane 35. The device also initially comprises a body 650 made of a meltable compound initially closing off this channel at its end opening into the reservoir 32.

With reference to FIG. 6B, the operating principle is as follows:

Initially, at room temperature, i.e. below the melting point T2 of the meltable compound used, the body 650 closes off the channel, and in the absence of heat, the membrane 35 is initially in its open position, and hence fluid may flow freely between the two channels 36, 37 (FIG. 6B—P100).

The heating module M4 is activated, to heat the volume of air 38 to the temperature T2, allowing the volume of air to dilate and the body 650 of the meltable material to melt. The dilation of the volume of air allows the body of molten meltable compound to be pushed towards the space 660, the body then depositing on the deformed membrane 35 (FIG. 6B—P200). The dilation of the volume of air also deforms the membrane 35 towards its closed position, closing off the passage between the two channels 36, 37. Through its dilation, the volume of air 38 may tend to press the meltable compound against the surface of the membrane.

After cooling, at the temperature T3 below the temperature T2, the meltable compound hardens and blocks and maintains the membrane 35 in its closed position, allowing the reaction chamber 30 to be sealed (FIG. 6B—P300).

Figure 7A:
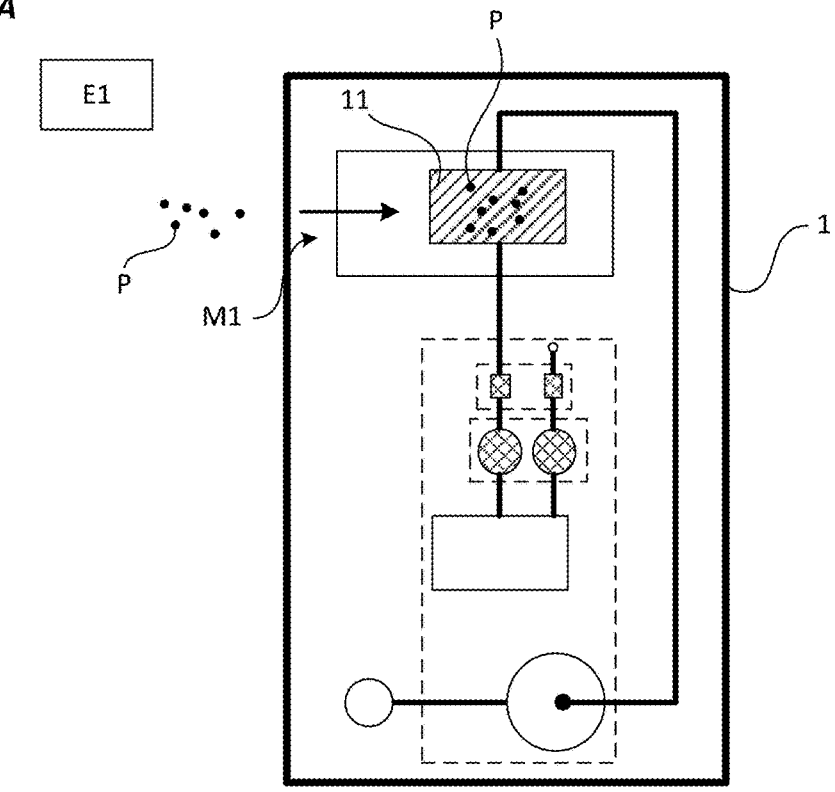
FIGS. 7A to 7F illustrate the various steps of the method according to the invention.

With reference to FIGS. 7A to 7F, the various steps of operation of a system using the isolating device 31 and the first variant of the sealing device 310 will now be defined below:

E1—FIG. 7A: the eluent reservoir 20 is placed under pressure with the elution liquid 24 and maintained under pressure by the plug formed by the first meltable compound 25. This reservoir 20 may notably be pre-filled in the component. The pre-filling may be carried out in the factory and the component then kept at a suitable storage temperature. Users are thus provided with a ready to use component.

Figure 7B:
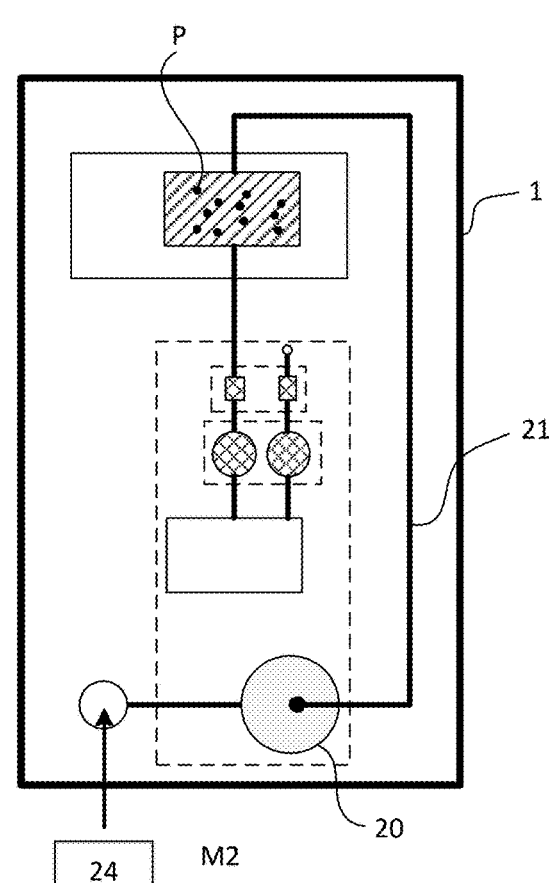

E2—FIG. 7B: precipitating airborne particles in the precipitating module M1. The airborne particles P are attracted towards the collecting electrode and are for example trapped on a membrane 11. This step is optional because the particles could be precipitated outside of the component and the sample placed in the module M1 located in the component 1.

Figure 7C:
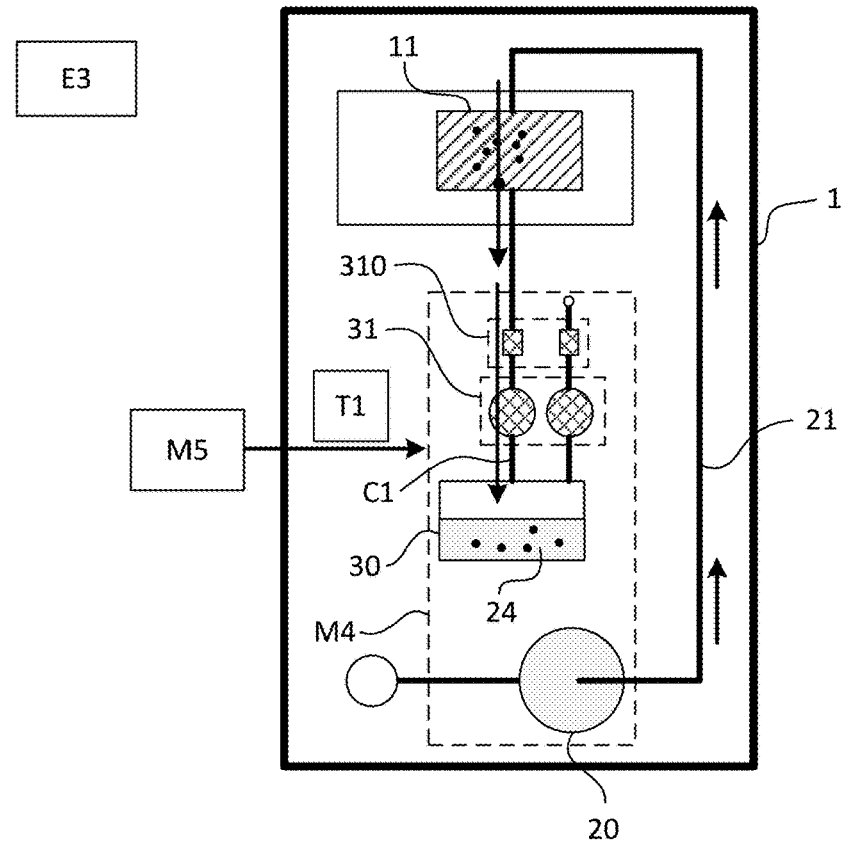

E3—FIG. 7C: activating the heating module M4 with a view to reaching a temperature having a first value T1 that is higher than the melting point of the first meltable compound 25 initially closing the eluent reservoir, but lower than the melting point of the bodies 350 employed in each cold sealing valve 330*a*, 330*b* of the reaction chamber 30. The control module M5 therefore activates the heating module M4. The reservoir 20 initially being under pressure, the elution liquid 24 is released from the reservoir through the elution fluidic channel 21 and reaches the precipitating module M1 where it detaches the particles attached to the membrane 11. The elution liquid 24, containing the particles P, flows through the elution fluidic circuit C1 and reaches the reaction chamber 30. The isolating device 31 and the sealing device 310 are open, allowing the liquid 24 to reach the reaction chamber 30.

Figure 7D:
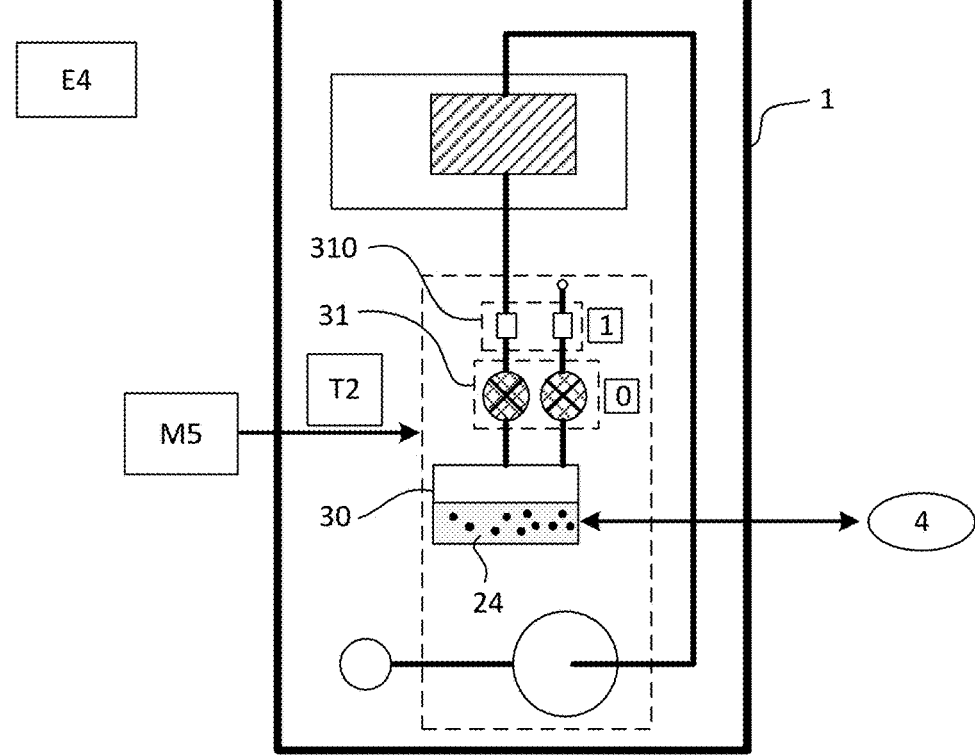

E4—FIG. 7D: the detection reaction is performed in the reaction chamber 30. Conventionally, the reaction requires the chamber to be heated. The control module M5 therefore activates the heating module M4. The heating module M4 is activated, allowing the reaction chamber to be heated to a second temperature value T2 required to achieve the biochemical reaction. This second temperature value is higher than the first temperature value T1. As indicated above, heating to the second temperature value is enough to cause:

dilation of the air present in the reservoir 32 of the first access-controlling device 31 so as to actuate the two hot isolating valves 33*a*, 33*b* of the reaction chamber 30 and to isolate the chamber during the reaction (valves in state 0);

dilation of the air bubble 340 used in the two valves 330*a*, 330*b*;

the second meltable compound used in the two cold sealing valves 330*a*, 330*b* of the second access-controlling device 310 to melt (valves in state 1).

Since the chamber 30 has been hot isolated through closure of the two isolation valves of the first fluidic-access-controlling device 31, the reaction may be performed in the chamber 30. The temperature required for the reaction may be identical to the temperature required to isolate the chamber, allowing the two effects to be combined: the reaction is driven and the chamber isolated merely by activating the heating module M4 once and controlling it to a single set point so as to achieve the desired temperature.

The amplification reaction (which is for example a PCR reaction or equivalent) may use means 4 capable of detecting an optical signal, due to fluorescence or electrochemiluminescence or a change in colour or even the formation of crystals, through a wall or the walls of the reaction chamber, or an electrochemical signal, with a view to detecting biological material in the chamber 30.

Figure 7E:
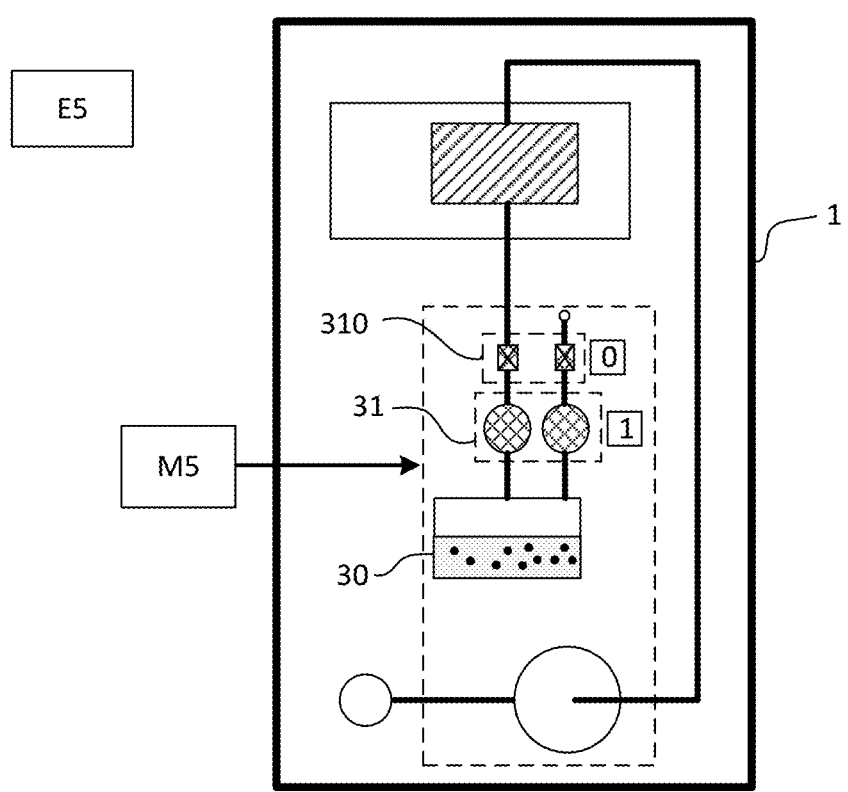

E5—FIG. 7E: once the reaction has ended, the heating module M4 is deactivated or commanded to a temperature value lower than said temperature value T2. This causes the membrane 35 of each hot isolation valve 33 to release (valve in state 1) and the second meltable compound used in the cold sealing valves 330*a*, 330*b* of the second fluidic-access-controlling device 310 to cool. Cooling occurs to a temperature having a value lower than said temperature value T2. The bodies 350 of the cold sealing valves set and close off the channels of the two fluidic circuits, sealing the reaction chamber 30 (valves in state 0). Automatic sealing of the chambers 30 via solidification of a compound in the channels connecting the chamber 30 to the exterior allows the component 1 to be removed from the instrument commanding it. Measurement of the (optical or electrochemical) signals emitted by the reaction products may be carried out in parallel.

Figure 7F:
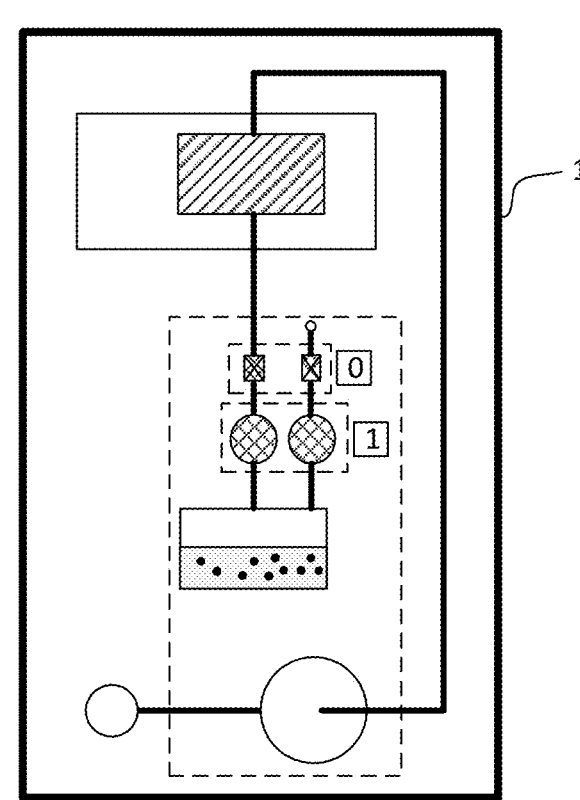

E6—FIG. 7F: the component 1 is hermetically sealed, allowing it to be handled or removed without risk of contamination of the instrument and of the environment. It will be noted that the passive operation of the sealing valves guarantees, should a mistake be made during handling or the instrument malfunction, that the reaction chambers will be sealed. The presence of biological material may require specific measures to be taken during removal.

Figure 8:
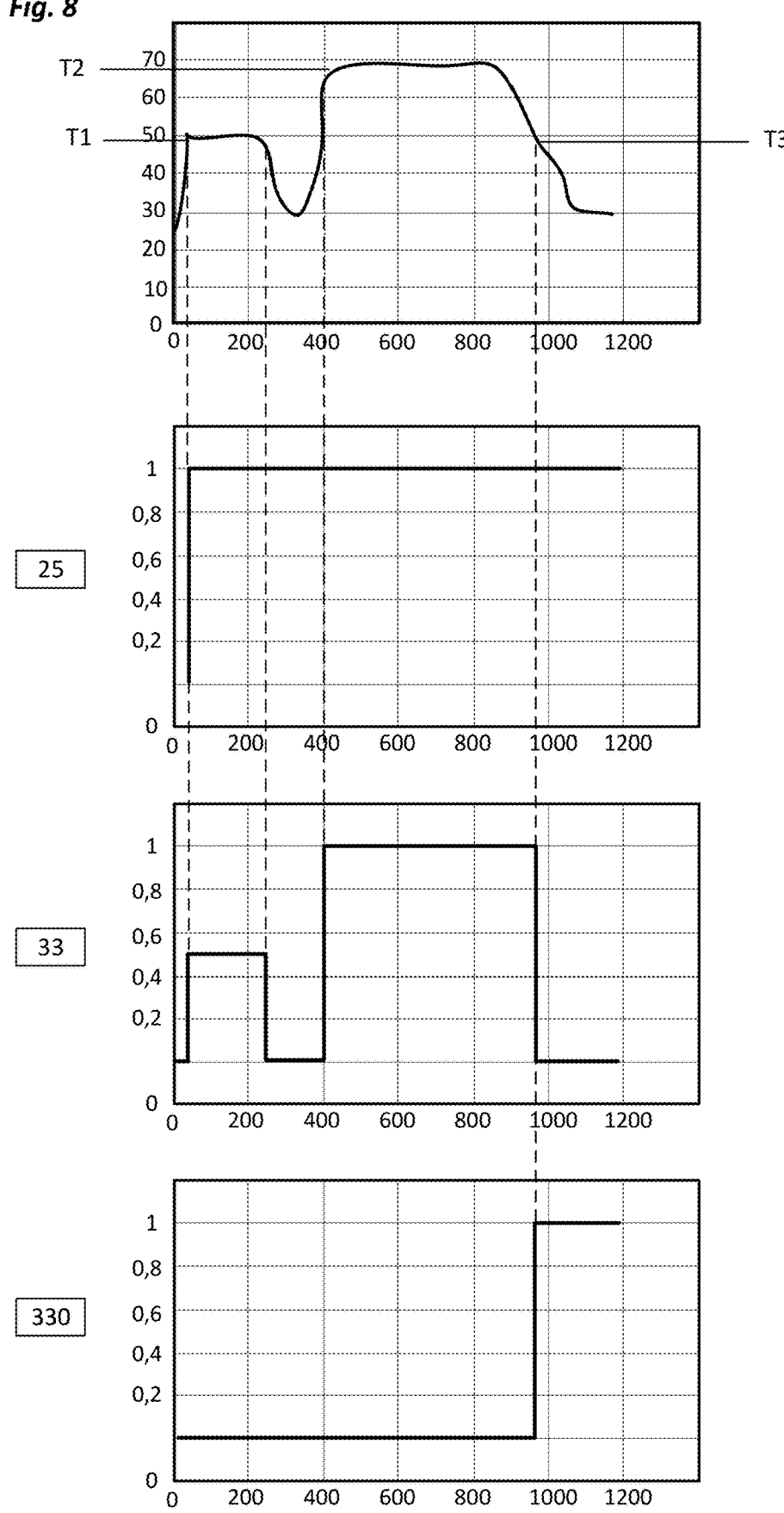
FIG. 8 shows a number of graphs illustrating the temperature cycling in correlation with the state taken by each valve employed in the component of the invention.

FIG. 8 illustrates how the valves are driven through temperature cycling applied to the component.

Thus, the following are shown in FIG. 8:

A first increase in temperature to a first plateau at a first value T1 (about equal to 48° C.), causing the first meltable compound 25 to melt in the eluting module and the elution liquid to be released. The temperature is too low to cause the valves 33 and 330 to close.

The heating module M4 is then deactivated or commanded to a low temperature, allowing the component to cool;

The heating module M4 is then made to rise to a second temperature plateau, having a value T2 (about equal to 70° C. for an amplification reaction carried out by LAMP) that is higher than the value of the first plateau. At this temperature plateau, the membranes of the two hot isolation valves 33 close, allowing the reaction chamber 30 to be isolated, and the second meltable compound melts, thus allowing the two cold sealing valves to be triggered. The second temperature plateau corresponds to that used to drive the detection reaction in the chamber 30. It is maintained long enough for this reaction to complete.

After this second plateau, the heating module M4 is deactivated or adjusted to a lower value T3, causing the component 1 to cool and the bodies 350 made of the second meltable compound to set, such that said bodies close off the two fluidic circuits C1, C2 and seal the cold reaction chamber 30, by closing the two valves 330.

The operating principle is identical with the second variant embodiment of the sealing device 610, which is illustrated in FIG. 6B.

Non-limitingly, the component 1 may take the form of a micro-fluidic chip formed from a stack of a plurality of layers. The stack may notably comprise three substrates each made of a material such as COP/COC (cyclic olefin polymer/cyclic olefin copolymer), polycarbonate or PMMA (polymethyl methacrylate). It may notably be sufficiently transparent to be read optically when the analysis is performed directly in the component. A membrane common to the various modules of the component may be inserted between the two substrates. The membrane is formed from a material that is very elastically deformable, allowing it to return to its initial shape after deformation. By way of example, the membrane may notably be made of materials such as elastomers of the silicone family, such as MQs (methyl-polysiloxanes), VMQs (vinyl-methyl-polysiloxanes), PVMQs (phenyl-vinyl-methyl-polysiloxanes) or thermoplastic elastomers (TPEs), for example TPE-Ss, TPSs, TPE-Es, TPCs. It thus plays the role of the deformable membrane that pushes the elution liquid in the eluting module and of the membranes used in the hot isolation valves of the isolating device 31.

The various fluidic circuits of the component 1 and the eluent reservoir 20, the air reservoir 32 of the first access-controlling device 31 and the reaction chamber 30, may be produced by machining or another process applied to one and/or two of the substrates of the component.

The heating module M4 of the instrument, which makes contact with the component 1, may for example be composed of a single resistive heater or of a heating element the temperature of which may easily be adjusted, such as a thermoelectric module. The heating module M4 is advantageously common to a plurality of modules of the component, notably:

the eluting module M2, in order to make the first meltable compound initially closing the eluent reservoir melt;

the analysing module M3, in order:

to actuate the membranes 35 of the two hot isolation valves 33, via dilation of the air stored in the reservoir 32;

to dilate the air bubble 340 employed in each cold sealing valve 330;

to make the second meltable compound employed in the two cold sealing valves 330 melt;

to ensure the reaction (for example the amplification reaction) occurs in the reaction chamber 30.

A temperature-regulating system may be employed to manage the temperature to which the heating module heats. This system may comprise at least one temperature sensor and a regulation loop executed by the control module.

Figure 9:
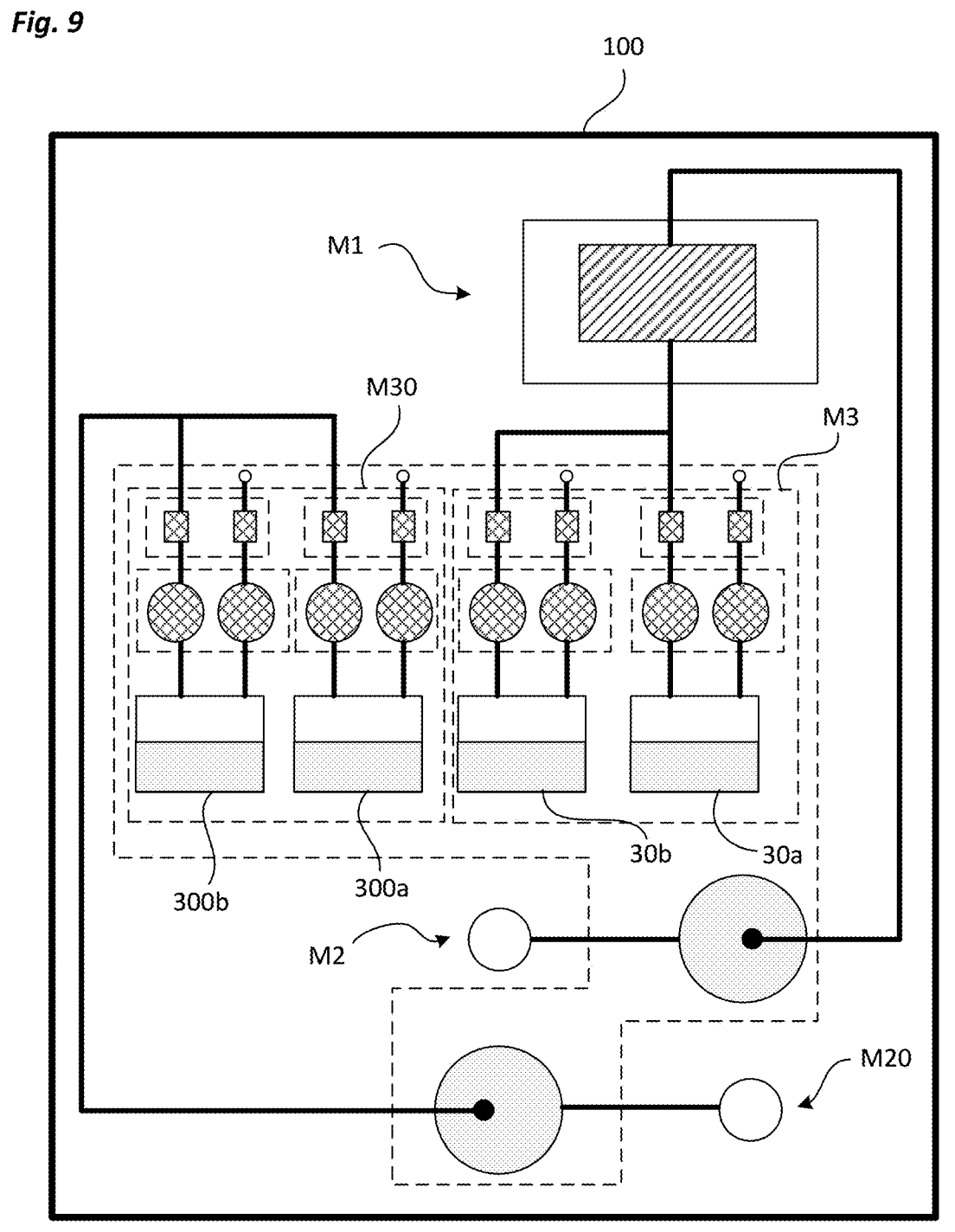

In one particular embodiment of the component 100, shown in FIG. 9, the analysing module M3 of the component 100 may comprise two parallel reaction chambers 30*a*, 30*b*. Furthermore, the component 1 may also comprise a module M6 for controlling the reaction, which comprises a second eluting module M20 and a second analysing module M30, the eluting module M20 having an architecture identical to that described above, with the exception that its fluidic circuit does not open into the precipitating module M1 but directly into two parallel control chambers 300a, 300b of the second analysing module M30. The second analysing module M30 has an architecture identical to that described above and receives elution liquid free of any particle, so as to perform control reactions.

The first eluting module M2 is used to elute the particles captured on the membrane 11, the particles P being conveyed to the two parallel chambers of the first analysing module M3. The second eluting module M20 serves to inject the eluent into the two control chambers 300a, 300b directly. The aim of these chambers is to verify that the analysis is being carried out correctly. One of these chambers contains a defined amount of the molecule to be detected (positive control) and will return, if the elution circuit works and if the reagents and the biological elements are intact, a positive signal. The other chamber serves as negative control and notably aims to verify that the system has not been contaminated, and that the measurement device is correctly calibrated. Since the two analysing modules M3, M30 (one for the sample and one for the controls) are located on a single heating module and since temperature is the only variable influencing the elution, the controls are, under these circumstances, good indicators of correct elution and of correct analysis.

The component for precipitating and analysing airborne particles has a number of advantages, among which:

the ability to incorporate all the modules into the same component, allowing a device that is simple to handle, perfectly autonomous and easily deployable to be manufactured;

the ability to control all the steps without physical connections such as pneumatic connections, mechanical links, etc. The component 1 is inserted into an instrument that controls the collecting module M1 by means of two electrical contacts and the modules M2 and M3 by means of a heated area;

the ability to use only a single heating module M4, common to the entire component, to carry out all the steps of the process of reagent injection, sample transfer and analysis;

a single fluidic component may be produced in the form of an easy to handle chip;

the ability of an operator to easily perform in succession a plurality of precipitations and analyses without having to decontaminate the precipitator, parts joining the precipitator and the sample-preparing module and the analysing module. Since the instrument commanding the component 1 does not make contact with the samples and with the biological reagents, it is immediately available for new precipitations and analyses.

It is notably possible for the solution to be based, to a large extent, on use of various paraffin waxes (linear alkanes) that melt at different, precise temperatures comprised for example between 40 and 70° C., for example docosane (42-45° C.), tetracosane (49-52° C.) or dotriacontane (65-70° C.).

The invention claimed is:

1. A method for collecting and analysing airborne particles, comprising:

precipitating particles from air on a collecting surface;

injecting a first reservoir with elution liquid to store the elution liquid in the first reservoir under pressure resulting from the injecting, an outlet of the first reservoir being blocked by a first meltable compound;

heating the first reservoir containing the elution liquid to a first temperature value to melt the first meltable compound;

conveying, via the pressure of the first reservoir, the elution liquid through an elution fluidic circuit to the collecting surface;

conveying the elution liquid along with the precipitated particles through the elution fluidic circuit to a reaction chamber of an analysis module;

heating the reaction chamber to a second temperature value higher than the first temperature value, so as to activate a detection reaction in said reaction chamber;

isolating said reaction chamber during the detection reaction by melting a second meltable compound and sealing said reaction chamber by setting the second meltable compound when the temperature drops to a third temperature value lower than said second temperature value; and analyzing the airborne particles collected in the reaction chamber.

2. The method according to claim 1, further comprising controlling the detection reaction by injecting a second elution liquid into at least one control chamber identical to said reaction chamber.

3. The method according to claim 2, wherein each elution liquid contains reagents.

4. The method according to claim 1, wherein the detection reaction is a biomolecular-amplification reaction.

5. The method according to claim 1, wherein isolating the reaction chamber includes closing via a deformable membrane, a first isolation valve arranged in the elution fluidic circuit.

6. The method according to claim 5, wherein sealing the reaction chamber includes releasing the second meltable compound into the elution fluidic circuit.

7. The method according to claim 5, wherein sealing the reaction chamber includes releasing the second meltable compound so that the second meltable compound deposits on the deformable membrane of the first isolation valve.

\* \* \* \* \*